(12) United States Patent
Shin

(10) Patent No.: US 10,907,146 B2
(45) Date of Patent: Feb. 2, 2021

(54) NUCLEIC ACID EXTRACTION METHOD USING SOLID SUBJECT

(71) Applicant: INFUSION TECH, Anyang-si (KR)

(72) Inventor: Yong Shin, Seoul (KR)

(73) Assignee: INFUSION TECH, Anyang-si (KR)

( * ) Notice: Subject to any disclaimer, the term of this patent is extended or adjusted under 35 U.S.C. 154(b) by 0 days.

(21) Appl. No.: 16/302,093

(22) PCT Filed: May 15, 2017

(86) PCT No.: PCT/KR2017/005019
§ 371 (c)(1),
(2) Date: Nov. 15, 2018

(87) PCT Pub. No.: WO2017/200249
PCT Pub. Date: Nov. 23, 2017

(65) Prior Publication Data
US 2019/0270979 A1    Sep. 5, 2019

(30) Foreign Application Priority Data

Dec. 21, 2016  (KR) .................. 10-2016-0175710

(51) Int. Cl.
*C12N 15/10*  (2006.01)
*C12Q 1/6806*  (2018.01)
*B01L 3/00*  (2006.01)

(52) U.S. Cl.
CPC ....... *C12N 15/101* (2013.01); *C12N 15/1006* (2013.01); *C12Q 1/6806* (2013.01); *B01L 3/502753* (2013.01)

(58) Field of Classification Search
CPC .................................................. C12N 15/101
See application file for complete search history.

(56) References Cited

U.S. PATENT DOCUMENTS 9,856,520 B2 * 1/2018 Shin .................. C12N 15/1006
2007/0196833 A1 8/2007 Gjerde
2015/0322486 A1 11/2015 Shin et al.

FOREIGN PATENT DOCUMENTS

KR   10-2015-0096444 A   8/2015

OTHER PUBLICATIONS

Jin et al., "Use of Dimethyl Pimelimidate with Microfluidic System for Nucleic Acids Extraction without Electricity," Analitical Chemistry, 89, 7502-7510 (2017); supplied by applicant.*
International Search Report for PCT/KR2017/005019 dated Aug. 8, 2017 from Korean Intellectual Property Office.
Shin, Y. et al., "Dimethyl adipimidate/Thin film Sample processing (DTS); A simple, low-cost, and versatile nucleic acid extraction assay for downstream analysis", Scientific Reports, 2015, vol. 5, article No. 14127, internal pp. 1-11.
Shin, Y. et al., "Solid phase nucleic acid extraction technique in a microfluidic chip using a novel non-chaotropic agent: dimethyl adipimidate", Lab on a Chip, 2014, vol. 14, No. 2, pp. 359-368.
Suter, J .D. et al., "Label-free DNA methylation analysis using opto-fluidic ring resonators", Biosensors and Bioelectronics, 2010, vol. 26, No. 3, pp. 1016-1020.

* cited by examiner

*Primary Examiner* — Lawrence E Crane
(74) *Attorney, Agent, or Firm* — Revolution IP, PLLC

(57) ABSTRACT

The present invention relates to a ribonucleic acid (RNA) extraction method using a solid subject, the method including activating a subject with a reactive amine group, injecting a sample having $1\times10^1$ to $1\times10^3$ cells/ml and a dimethyl suberimidate (DMS) compound or a dimethyl pimelimidate (DMP) compound into the subject, and forming a complex having the RNA within the sample and the compound, and extracting the RNA by treating elution buffer to the subject on which the complex is formed. The subject, particularly, the thin film device used for extracting the RNA, has improved hydrophilicity compared to the conventional silicon substrate, so that RNA is extracted more efficiently.

5 Claims, 10 Drawing Sheets

[FIG. 3]
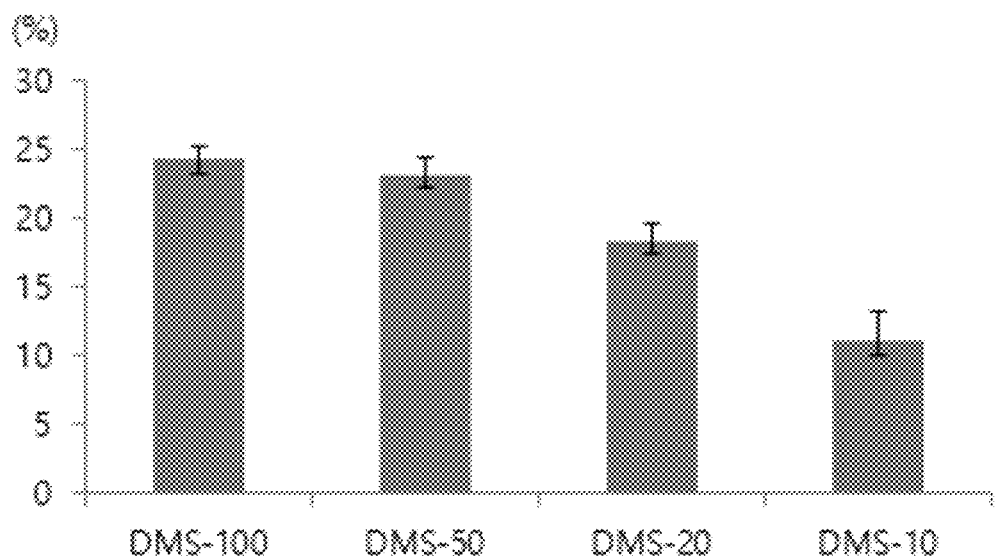
[FIG. 4]
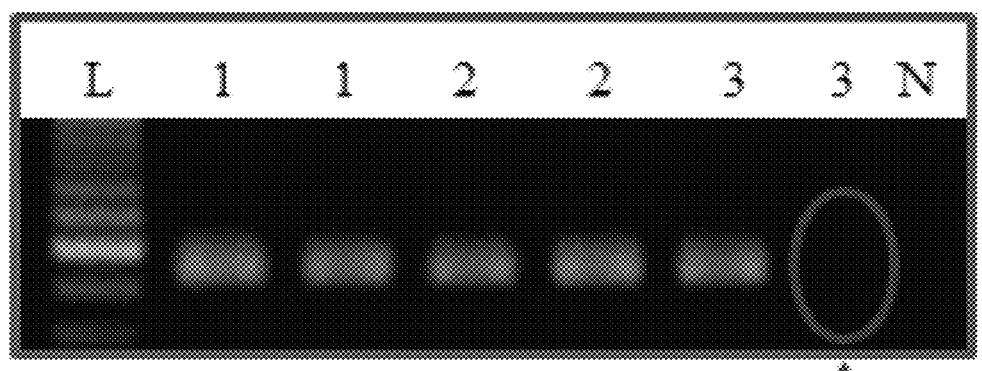
1: Qiagen kit #1 (ratio: 2.04)
1: Qiagen kit #2 (ratio: 1.94)
2: DMS #1 (ratio: 1.72)
2: DMS #2 (ratio: 1.76)
3: DMA #1 (ratio: 1.79)
3: DMA #2
N: negative

[FIG. 5]
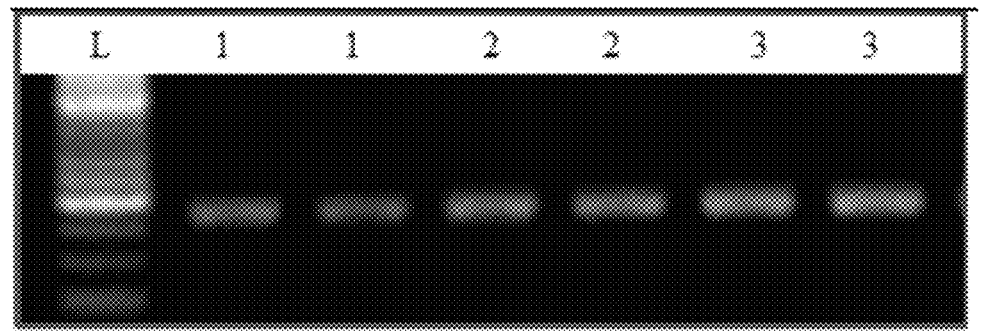
1: No Chem #1;  1: No Chem #2
2: DMA #1;  2: DMA #2
3: DMS #1;  3: DMS #2
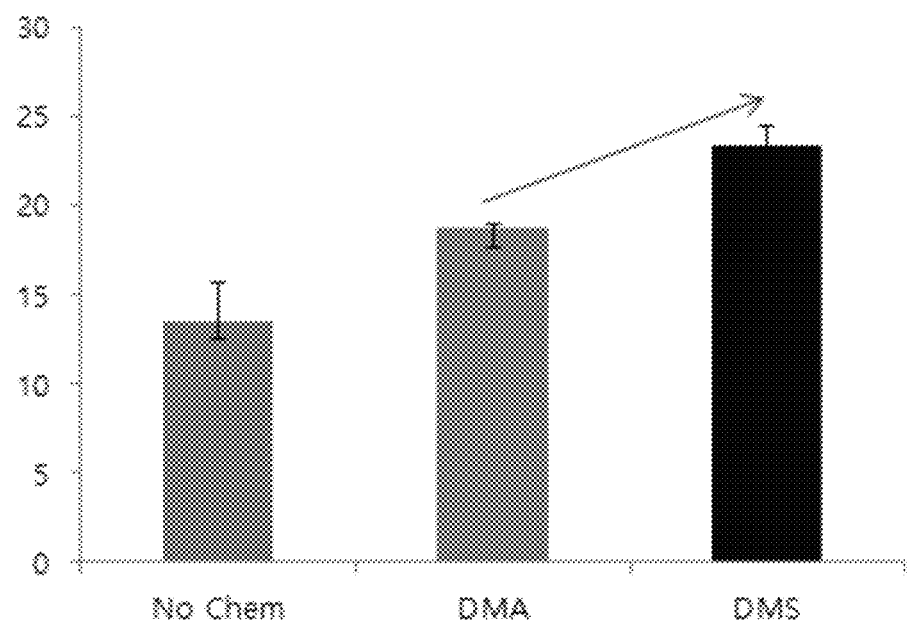

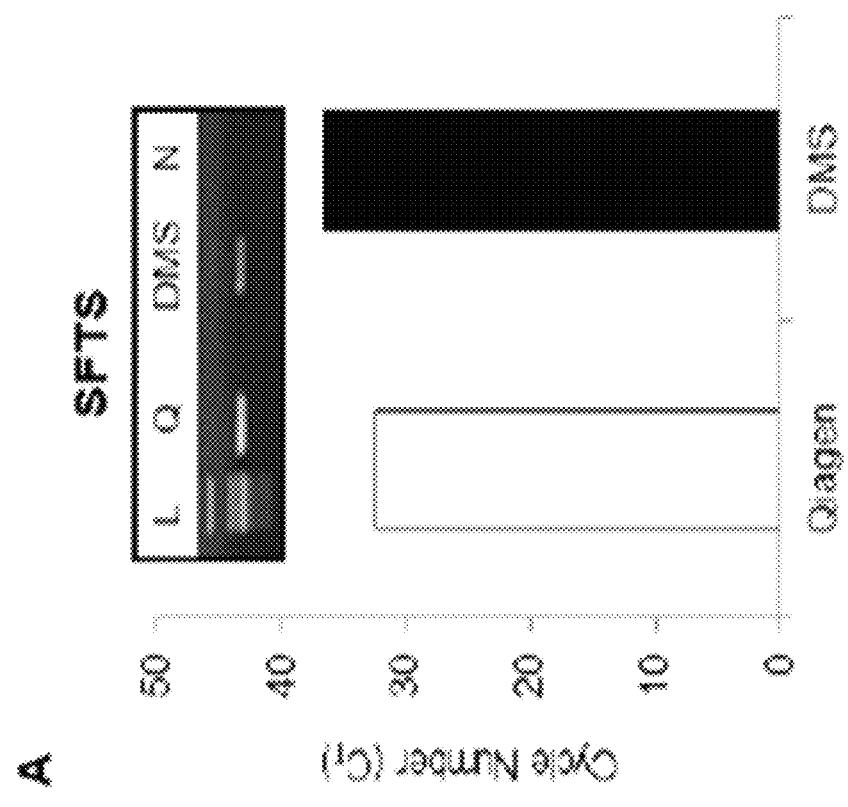
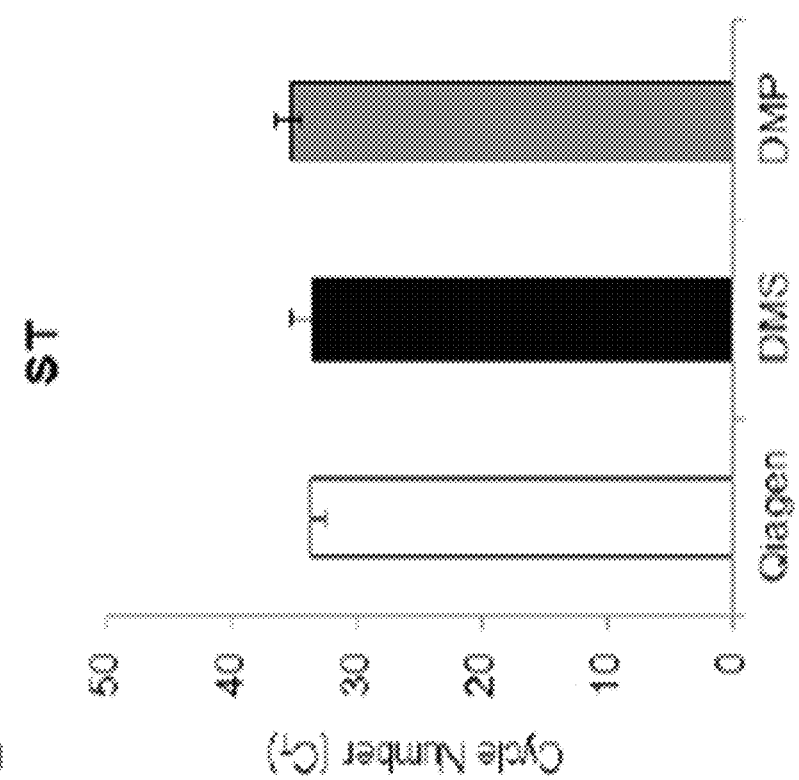
FIG. 10

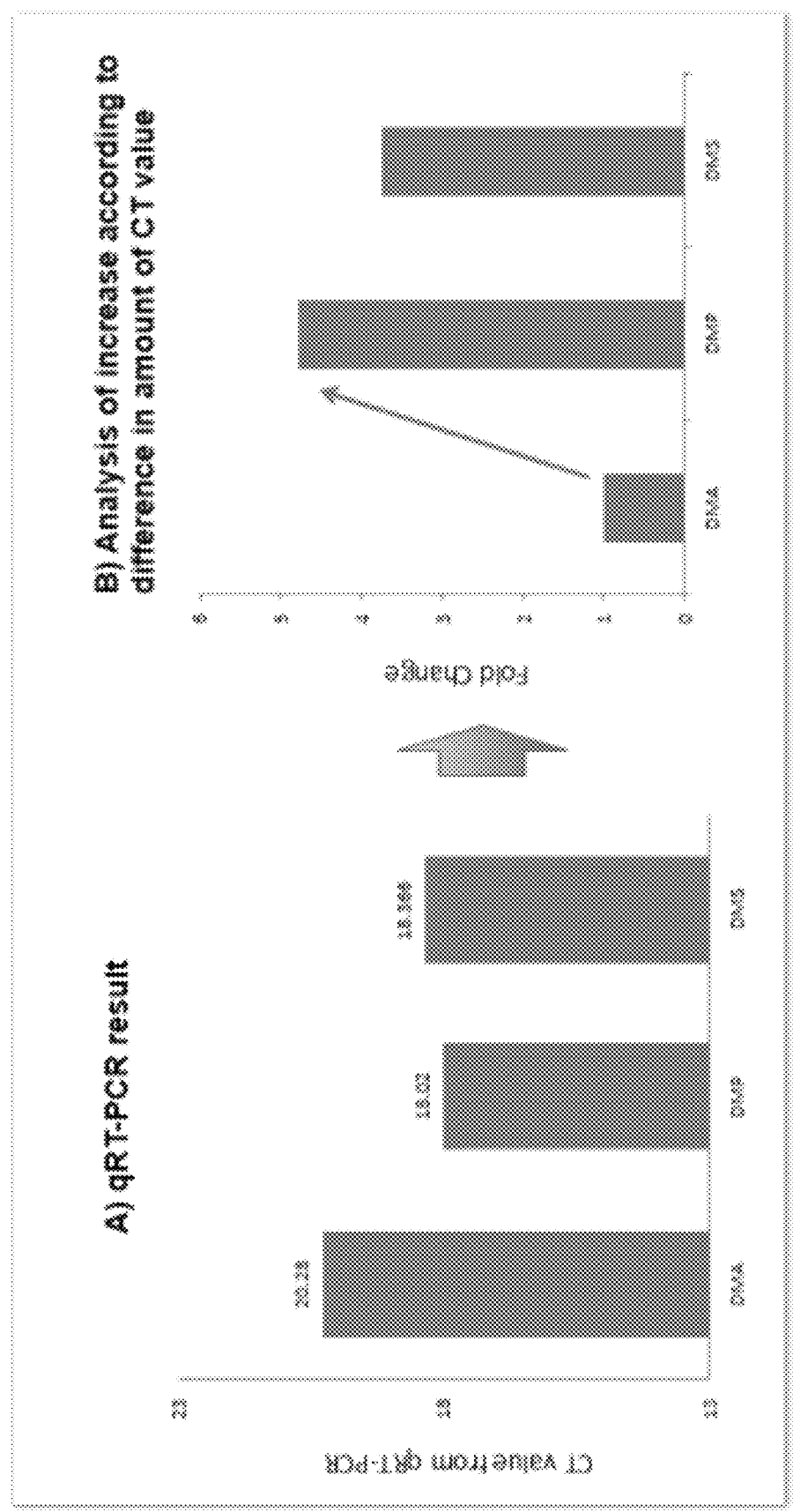
[FIG. 11]

NUCLEIC ACID EXTRACTION METHOD USING SOLID SUBJECT

CROSS REFERENCE TO PRIOR APPLICATIONS

This application is a National Stage Application of PCT International Patent Application No. PCT/KR2017/005019 filed on May 15, 2017, under 35 U.S.C. § 371, which claims priority to Korean Patent Application Nos. 10-2016-0060310 and 10-2016-0175710 filed on May 17, 2016 and Dec. 21, 2016, respectively, which are all hereby incorporated by reference in their entirety.

TECHNICAL FIELD

The present invention relates to a method of extracting nucleic acids using solid subject, and more particularly, to a method for extracting nucleic acids from a nucleic acids source including various eukaryotic cells, bacterial cells, virus cells or body fluids by a simple method.

BACKGROUND ART

Nucleic acids are an important analytical tool for identifying disease states, and DNA biomarkers such as single nucleotide polymorphisms (SNPs), mutations or DNA methylation, help researchers to find the cause of cancer, diagnose and observe the condition of the disease during the early stages of the disease, as well as provide important clues for great opportunities of prognosis and monitoring.

Because nucleic acids such as DNA are present at very low physiological concentrations compared to other components such as proteins (e.g., tens of nanograms of DNA versus tens of micrograms of protein per microliter of whole blood), efficient extraction of DNA from clinical samples and pre-concentrating is very important for subsequent processes such as amplification and detection. In the case of methylated DNA, this problem is more important.

DNA methylation plays a crucial role in regulating gene expression and chromatin organization in normal eukaryotic cells. DNA methylation occurs by the covalent addition of a methyl group onto the 5-carbon of the cytosine ring and produces 5-methylcytosine. These methyl groups protrude into the major groove of DNA and effectively inhibit transcription.

In mammalian DNA, 5-methylcytosine is found in about 4% of genomic DNA, mainly in cytosine-guanosine dinucleotides (CpGs). Such a CpG site occurs less than the expected frequency in the total human genome, but is more frequently found in small-length DNA, referred to as CpG islands.

These islands are typically found in or near the promoter region of the gene, where transcription begins. Unlike genomic DNA, which is mostly methylated at CpG sites, CpG islands in germ-line tissue and normal somatic promoters remain unmethylated, leading to gene expression.

DNA methylation is mediated by a highly related group of DNA methyltransferase enzymes (DNMT), which transfer methyl groups from S-adenosyl-L-methionine to cytosine in CpG dinucleotides. The methyl-cytosines established by DNMTs act as binding sites for the methyl-CpG binding domain (MBD) proteins MeCP2, MBD.

MBDs translate methylated DNA chromatin environment which is oppressive for transcription and compacted, through interaction with histone deacetylase, histone methyltransferase and ATP-dependent chromatin remodeling enzymes. In particular, MBD is the methyl CpG-binding domain of the MeCP2 protein, which binds to symmetrically methylated CpGs in any sequence and participates in mediating methylation-dependent transcriptional repression. Although there is strong evidence that MeCP2 binds to exclusively methylated DNA fragments in vivo, the DNA methylation-independent binding activity of MeCP2 in vitro is also documented in agreement, which can be used appropriately for general in vitro DNA analysis.

Recently, the use of high purity purified nucleic acids has been increasing in various fields such as biotechnology, diagnostic medicine, drug medicine and metabolic medicine, so efforts have been continuing to separate nucleic acids more rapidly and more purely from various biological samples.

However, technology relating to a carrier which specifically adsorbs only nucleic acids from various substances contained in a cell lysis solution such as genomic DNA, plasmid DNA, messenger RNA, proteins, cellular debris particles, has been developed very greatly among the methods of separating nucleic acids so far and almost all the research has been focused on the research and development of materials adsorbing nucleic acids.

Therefore, in order to isolate nucleic acids more rapidly and purely, it requires more than anything to develop a technology capable of separating desired nucleic acids only rapidly from cell debris particles, protein denaturation aggregates and various other cell degradation substances.

DISCLOSURE

Technical Problem

It is an object of the present invention to provide a method of extracting nucleic acids and an apparatus thereof which can extract large amount and high purity of nucleic acids from various nucleic acids sources simply and with low cost, compared to the method of extracting nucleic acids using all the commercialization kits requiring large equipment (centrifuge and magnet, etc.) for nucleic acids extraction including conventional Qiagen.

Technical Solution

In order to solve the above problems, the present invention provides a method of extracting nucleic acids comprising: modifying by introducing an amine group into an subject (step 1); forming a complex of the nucleic acids and a compound by injecting a nucleic acids sample and a compound represented by following Chemical Formula 1 onto a modified subject (step 2); and extracting the nucleic acids by treating elution buffer to the subject on which the complex is formed (step 3).

Also, the present invention provides a thin film device for extracting nucleic acids comprising: an upper thin film through which an inlet hole and an outlet hole pass, respectively; a lower thin film disposed apart from the upper thin film; a microchannel chamber in which a microchannel in which an inlet end and an outlet end respectively correspond to and communicate with an inlet hole and an outlet hole of the upper thin film, are formed in an inner pattern, and an injection path communicating with the inlet of the microchannel is formed adjacent to the inlet end, and which is disposed between the upper thin film and the lower thin film; and a sealing means for sealing each side of the upper thin film and the lower thin film to seal the microchannel chamber.

In addition, the present invention provides a composition for enhancing nucleic acids extraction efficiency comprising a compound represented by following Chemical Formula 1 as an active ingredient,

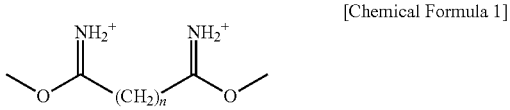

[Chemical Formula 1]

wherein n is an integer of 5 to 10.

Advantageous Effects

The method of extracting nucleic acids according to the present invention can easily and rapidly extract nucleic acids from various eukaryotic cells, bacterial and viral cells or nucleic acids sources including body fluids and also, the nucleic acids can be extracted more efficiently by improving the hydrophilicity compared to the conventional silicone substrate, using thin film device for nucleic acids extraction.

DESCRIPTION OF DRAWINGS

FIG. 3 is a graph showing the DNA extraction efficiency according to the concentration of dimethyl suberimidate (DMS).

FIG. 4 is a graph showing the results of DTS analysis according to the present invention and conventional Qiagen kits using breast cancer cells, and DNA extraction efficiency using dimethyl adipimidate (DMA), which is a compound similar to DMS used in DTS analysis.

FIG. 5 is a graph showing DTS analysis according to the present invention, and the PCR amplification efficiency of extracted DNA according to the analysis using DMA similar to DMS used in DTS analysis.

FIG. 10 shows validation of the HINT system in clinical samples. (A) Viral RNA extraction from the blood plasma of a severe fever with thrombocytopenia syndrome patient. (B) Bacterial DNA extraction from the blood plasma of a scrub typhus (ST) patient.

FIG. 11 shows the result of comparing DNA amplification efficiency when DMA, DMP or DMS is applied to the HINT system.

BEST MODE

Figure 1:
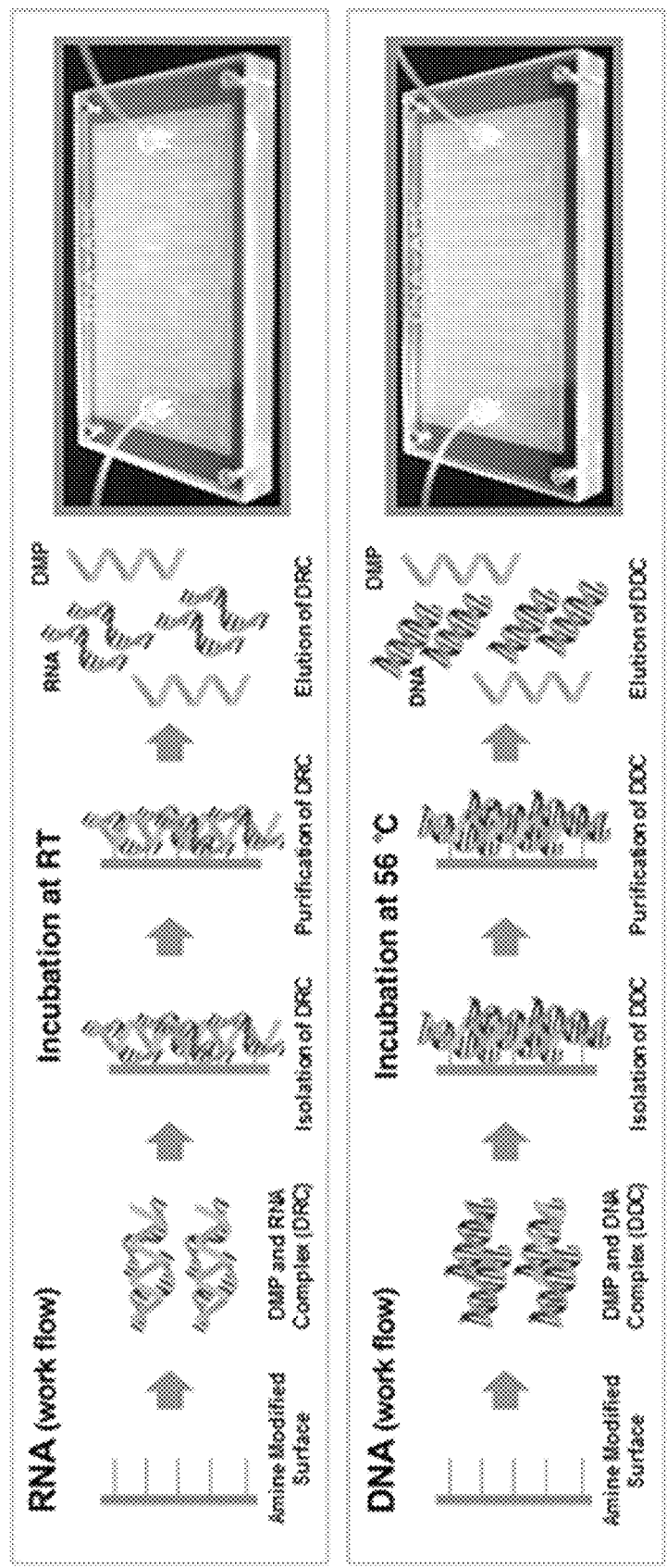
FIG. 1 is schematic representation of the principle of the HINT (homobifunctional imidoesters (HIs) for nucleic acids extraction using thin films) system for nucleic acids extraction.

Hereinafter, the present invention will be described in more detail.

The inventors of the present invention have developed an extraction method capable of separating and extracting nucleic acids from a nucleic acids sample and found that it can isolate nucleic acids with large amounts and high purity at a low cost and simpler than conventional methods of extracting nucleic acids, and perform diagnosis immediately on site without using large equipment by forming a complex of a nucleic acids sample and a compound represented by the following Chemical Formula 1 and completed the present invention.

The present invention relates to a method of extracting nucleic acids comprising: modifying by introducing an amine group into an subject (step 1); forming a complex of the nucleic acids and a compound by injecting a nucleic acids sample and a compound represented by following Chemical Formula 1 onto a modified subject (step 2); and extracting the nucleic acids by treating elution buffer to the subject on which the complex is formed (step 3),

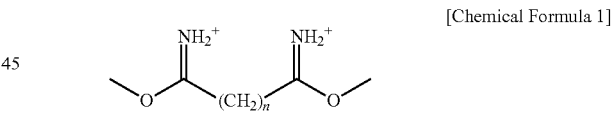

[Chemical Formula 1]

wherein n is an integer of 5 to 10.

Preferably, in the compound represented by the Chemical Formula 1, n is an integer of 5 to 7.

The subject may be any one of a thin film device, a magnetic bead or a nanoparticle, but it is not limited thereto.

The nucleic acids may include any one of DNA or RNA, but it is not limited thereto.

The nucleic acids may include methylated DNA, but it is not limited thereto.

The modification may be performed by introducing a silane compound in the subject, but it is not limited thereto.

The silane compound may be 3-aminopropyltriethoxysilane (APTES), but it is not limited thereto.

The present invention may further comprise washing the subject by plasma treatment before the step 1, but it is not limited thereto.

The present invention may further comprise washing the subject which the complex is formed between the step 2 and the step 3, but it is not limited thereto.

The nucleic acids sample may be a eukaryotic cell, a bacterial cell, a virus cell, a whole blood or a urine derived sample, but it is not limited thereto.

The present invention may further comprise a protease and an elution buffer on the subject modified in the step 2, but it is not limited thereto.

In addition, the present invention provides a thin film device for extracting nucleic acids comprising: an upper thin film through which an inlet hole and an outlet hole pass, respectively; a lower thin film disposed apart from the upper thin film; a microchannel chamber in which a microchannel in which an inlet end and an outlet end respectively correspond to and communicate with an inlet hole and an outlet hole of the upper thin film, are formed in an inner pattern, and an injection path communicating with the inlet of the microchannel is formed adjacent to the inlet end, and which is disposed between the upper thin film and the lower thin film; and a sealing means for sealing each side of the upper thin film and the lower thin film to seal the microchannel chamber.

The present invention may further comprise a first tubing adapter communicating with the inlet hole of the upper thin film and the inlet end of the microchannel; and a second tubing adapter communicating with the outlet hole of the upper thin film and the outlet end of the microchannel.

A compound represented by the following Chemical Formula 1 may be injected into the inlet end of the microchannel through the inlet hole of the upper thin film, and a nucleic acids sample may be injected through the injection path of the microchannel chamber,

[Chemical Formula 1]
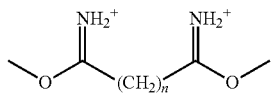

wherein n is an integer of 5 to 10.

Preferably, in the compound represented by the Chemical Formula 1, n is an integer of 5 to 7.

The microchannel may be patterned to be folded a plurality of times.

The microchannel may include a plurality of expanding portions having an expanded cross-section, and a plurality of reducing portions having a cross-section smaller than the expanding portion and the expanding portion and the reducing portion may be disposed alternately.

Hereinafter, the present invention will be described in detail with reference to the drawings of the present invention.

The nucleic acids analysis according to the present invention is a DTS (Dimethyl suberimidate/Thin film Sample) analysis of analyzing nucleic acids using DMS in a thin film device, and includes three steps of sample elution/culture, washing and elution, without centrifugation. For example, a thin film device is modified through 3-aminopropyltriethoxysilane (APTES) as a silane compound, and the hydrophobic thin film device is converted to hydrophilic by such modification.

A nucleic acids sample and an elution buffer and a DMS solution are injected onto the modified thin film device. A complex between the nucleic acids and the DMS can be formed using a cross-linking mechanism between the nucleic acids and the DMS by interaction of the amino group of the nucleic acids and the bifunctional amine group of the DMS, and the DNA can be extracted from the sample.

In addition, the present invention provides a composition for enhancing nucleic acids extraction efficiency comprising a compound represented by following Chemical Formula 1 as an active ingredient,

[Chemical Formula 1]
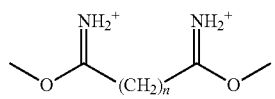

wherein n is an integer from 5 to 10.

Preferably, in the Chemical Formula 1, n is an integer of 5 to 7.

The composition may further comprise a protease and an elution buffer, and the nucleic acids may be DNA or RNA, but it is not limited thereto.

In addition, the present invention provides a kit for enhancing nucleic acids extraction efficiency comprising the composition.

Meanwhile, since the compound represented by the Chemical Formula 1 used in the present invention includes bifunctional imidoesters, it is also referred to as homobifunctional imidoesters (HIs) in the present specification, the HIs forms rapid and strong bonding with the nucleic acids to form a complex, and are captured on the surface of a subject modified with an amine-reactive group, thereby enabling highly efficient nucleic acids extraction.

[Chemical Formula 1]
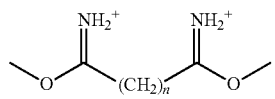

wherein n is an integer from 5 to 10.

Preferably, in the Chemical Formula 1, n is an integer of 5 to 7.

The HIs used in the present invention are dimethyl pimelimidate (DMP) and dimethyl suberimidate (DMS), and a comparative experiment was conducted using dimethyl adipimidate (DMA) which has similar chemical structure to the same. The chemical structures of DMP (Chemical Formula 2), DMS (Chemical Formula 3) and DMA (Chemical Formula 4) are as follows.

[Chemical Formula 2]
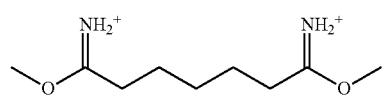

[Chemical Formula 3]
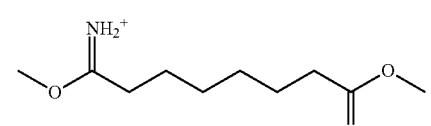

[Chemical Formula 4]
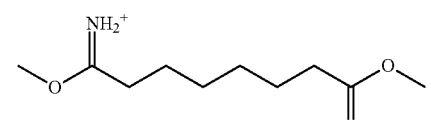

Hereinafter, the present invention will be described in detail with reference to the following examples. It should be noted, however, that the following examples are illustrative of the present invention and are not intended to limit the scope of the present invention. The examples of the present invention are provided to more fully describe the present invention to those skilled in the art.

<Example 1> Fabrication of Thin Film Device and Pretreatment

1. Thin Film Production

Figure 2:
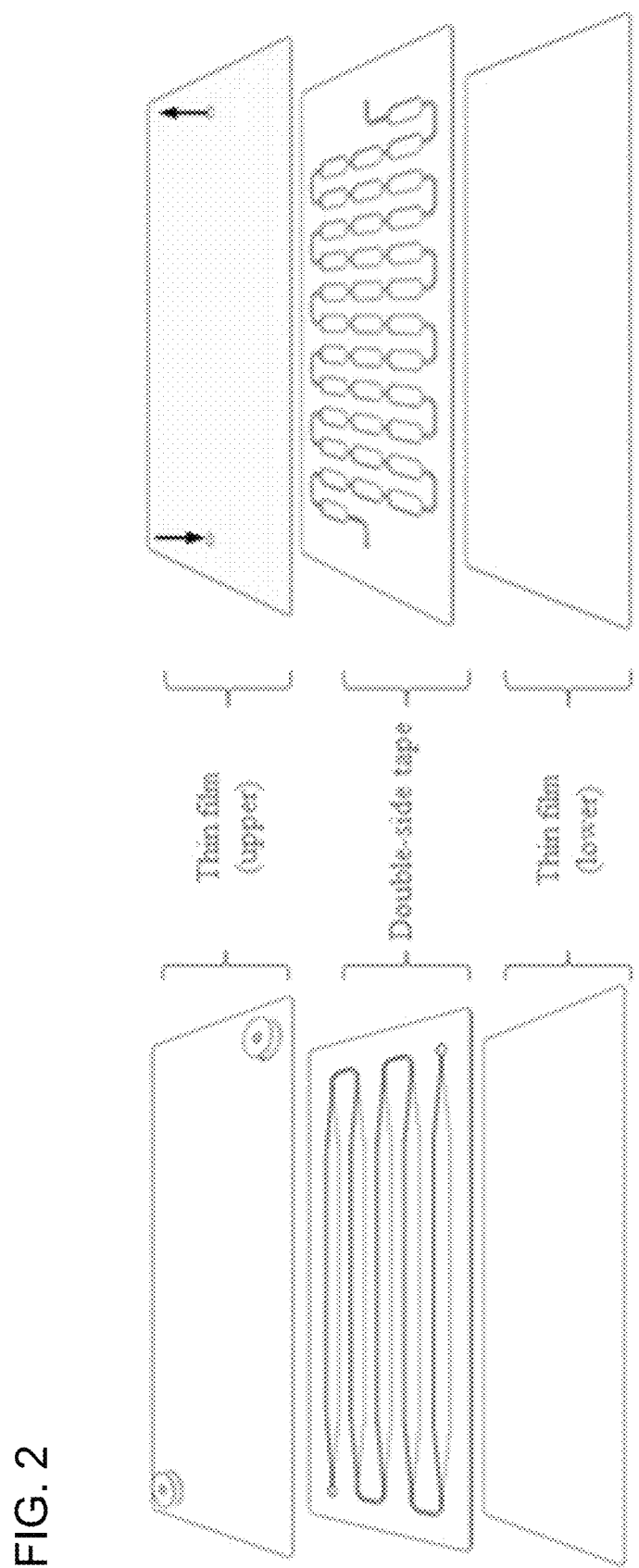
FIG. 2 is an exploded view showing a configuration of a thin film device.

The thin film device of the present invention was easily and quickly fabricated using a laser cutting device (Universal Laser Systems, Scottsdale, USA) (see FIG. 2). First, the thin film device is composed of an upper thin film and a lower thin film, and a microfluidic chamber inserted between the upper thin film and the lower thin film. The microfluidic chamber comprises a plurality of slot-type microwells interconnected by a flow path in a chamber for extracting DNA from a nucleic acids source.

To fabricate the microfluidic chamber, a microfluidic chamber design was cut with a laser cutting device on a 300 μm thick double-sided tape (100 μm thick polyester film sandwiched between a 100 μm thick double-sided tapes) to produce a microfluidic chamber. The thin films (upper and lower portions) were cut to the same dimensions as the microfluidic chamber using a laser cutting machine.

An inlet and an outlet, which are through holes, were fabricated in the upper thin film. The laser cutting thin films (upper and lower) were attached on the upper and lower surfaces of the laser-cutting microfluidic chamber, respectively, using a permanent adhesive. The height of the microfluidic chamber was about 300 μm and the total volume was 300 μl (300 μl volume, 8.4 cm×3.7 cm).

The tubing adapter for injecting the nucleic acids source was prepared by attaching a 3 mm thick cast acrylic sheet (MARGA CIPTA, Indonesia) to one side of the double sided tape and cutting and perforating with a laser cutting device. The prepared tubing adapter was attached to the inlet and the outlet of the microfluidic chamber, respectively. Thereafter, pre-cut tygon tubing (AAC02548; Cole-Parmer, Vernon Hills, USA) was placed in the hole of the adapter and sealed with epoxy.

The thin film device thus fabricated has advantage capable of treating nucleic acids samples of various capacities (100 μl, 300 μl and 500 μl).

2. Pretreatment of Thin Film Devices

To analyze DNA using the thin film device, the inside of the thin film device was treated with oxygen plasma for 10 minutes, and the plasma-treated thin film device was soaked in aqueous solution containing 2% 3-aminopropyltriethoxysilane (APTES) and then thoroughly washed with deionized water. After washing, to cure the thin film device, the washed thin film device was quickly dried under a nitrogen stream to modify the thin film device with an amine.

The water contact angle measurement of the amine-modified thin film device using Drop Shape Analyzer (DSA100, KRUSS, Germany) showed that the hydrophilicity of the thin film device changed significantly according to temperature and incubation time. After silanization of the thin film device with APTES at 65° C. for 10 minutes, the hydrophilicity of the thin film surface hydrophilicity increased (about 30-40° C.).

<Example 2> DTS (Dimethyl Suberimidate/Thin Film Sample) Analysis

In the present invention, the nucleic acids analysis method in which dimethyl suberimidate (DMS) is applied to the thin film device fabricated as described above is designated as DTS, and DTS analysis is performed in the following experiment.

Namely, the optimized analytical solution was prepared in order to extract DNA using the thin film apparatus (300 μl amount, 8.4 cm×3.7 cm) modified with amine previously. The optimized analytical solution was prepared by mixing elution buffer containing 100 mM Tris-HCl (pH 8.0), 10 mM EDTA, 1% SDS and 10% Triton X-100 in DMS (50 mg/mL), and as a nucleic acids analysis sample, 100 μl of each sample derived from cells, bacteria, blood or urine was mixed with 200 μl of the analytical solution.

The mixed solution of the mixed nucleic acids analysis sample and the analytical solution is introduced into the inlet of the upper substrate of the thin film apparatus modified with amine and the two amine groups of DMS are coupled with the DNA while the mixed solution is transferred into the microfluidic chamber, and the amine group modified in the thin film apparatus and DNA were combined to form a complex and separate the DNA. At this time, the thin film device was placed in one of an incubator maintaining at a constant temperature (56° C.) for 20 minutes or a thermoelectric cooler (TEC) including a controller (Alpha Omega Instruments) so as to sufficiently extract DNA from a nucleic acids analysis sample.

To remove foreign substances in the DMS-DNA complex, after washing with PBS buffer, DNA was extracted using elution buffer (10 mM sodium bicarbonate, pH 10.6). After measuring the amount and purity of the extracted DNA, the optical density ratio of the sample was determined at 260 nm (DNA) and 280 nm (protein) using Enspire Multimode Plate Reader (PerkinElmer). To compare the conventional DNA extraction method and the DTS analysis of the present invention, the QIAmp DNA mini kit was used according to a known method (Qiagen, Hilden, Germany).

As shown in FIG. 3, the DNA binding efficiency was confirmed according to DMS concentration, and it was confirmed that DNA binding efficiency was highest when DMS concentration was 50-100 mg/ml.

<Example 3> DNA Extraction from Eukaryotic Cells Using DTS Analysis

In a plastic culture plate of high glucose Dulbecco's modified eagle medium (DMEM, DMEM Life Technology) supplemented with 10% fetal calf serum (FCS) in a 5% $CO_2$ atmosphere, 37° C. humidified incubator, after culturing six eukaryotic cells (MCF-7 (breast), NCI-H1975 (lung), CaCo-2 (large intestine), T24 (bladder), U937 (lymphocyte) and Jurkat (peripheral blood)), DNA was extracted from the eukaryotic cells in the same manner as in Example 2, and proteinase K, protease, was treated to extract genomic DNA. And for comparison, DNA was extracted from eukaryotic cells using a QIAmp DNA mini kit.

End-point PCR and real time PCR were performed to confirm the amount and purity of DNA. Forward and reverse primers of some genes (HRAS, Actin and RARβ) were synthesized as a normal length of about 24 base pairs. End-point PCR was performed at an initial denaturation step at 95° C. for 15 minutes; 45 cycles of 95° C., 45 seconds, 59° C., 45 seconds (RARβ), and 72° C., seconds; and a final extension step at 72° C. for 10 minutes. 5 to 10 μl of the DNA was amplified in total volume of 25 μl containing 1×PCR buffer (Qiagen), 2.5 mM magnesium chloride ($MgCl_2$), 0.25 mM deoxynucleotide triphosphate, 25 pmol of each primer, and 1 unit of Taq DNA polymerase. For real-time PCR analysis, the following steps were modified as described in LightCycler 2.0 (Roche Diagnostics) as follows. 5 to 10 µl of DNA was amplified in total volume of 20 µl containing 4 µl of LightCycler FastStart DNA Master mix, 25 pmol of each primer, 2 µl of 1×PCR buffer (QUEAGEN), 2.5 mM magnesium chloride (MgCl$_2$), 0.25 mM deoxynucleotide triphosphate, and distilled water. After first pretreatment at 95° C. for 10 minutes, 50 cycles of 95° C., 10 seconds, 58° C., 30 seconds (for HRAS and the actin gene), and 72° C. for 10 seconds were performed and then cooled at 40° C. for 30 seconds. Amplified products with SYBR green signal were performed in LightCycler 2.0 (Roche Diagnostics).

To investigate the epigenetic variation of RARβ from the extracted DNA, the DNA was digested with either a MspI or HpaII solution (150 µl) at 37° C. for 20 minutes in a single reaction tube. After the digestion step, the single reaction tube was left at 80° C. for 10 minutes for inactivation of the restriction enzyme. Following the inactivation process, the digested DNA was used as a template for epigenetic analysis of the RARβ gene obtained in quantitative analysis using conventional PCR.

On the other hand, as a result of comparing and analyzing the DNA extraction efficiency by the DTS analysis according to the conventional Qiagen kit, the DTS analysis according to the present invention using breast cancer cells, and the analysis using DMA which is a compound similar to DMS used in DTS analysis, shown in FIG. 4, in the analysis using DMS, DNA could be extracted from breast cancer cells in combination with DNA, whereas in the analysis using DMA (dimethyl adipimidate), DNA could not be extracted from breast cancer cells.

As shown in FIG. 5, PCR amplification efficiency of the DNA extracted using DMS was improved by 25% as compared with the analysis using DMA.

<Example 4> DNA Extraction from Bacterial Cells Using DTS Analysis

PCR-based DNA amplification was performed using DNA extracted using DTS analysis to confirm DTS assay performance in bacterial cells. All commercial primer of *Escherichia coli, Mycobacterium abscessus, Mycobacterium gordonae* and *Salmonella* Strains (*Salmonella typhimurium, Salmonella* spp. Newport, *Salmonella* Newport, and *Salmonella* Saintpaul) were used.

For the optimization reaction, elution buffer containing 100 mM Tris-HCl (pH 8.0), 10 mM EDTA, 1% SDS, 10% Triton X-100 and 20 mg/mL of lysozyme were mixed with DMS (50 mg/mL). PCR was performed to verify the validity of the DTS method of the present invention. *E. coli* XL1 blue strains were inoculated into 50 µg/ml of tetracycline and Luria-Bertani (LB) medium, cultured at 37° C. for one day in a shaking condition, samples of $10^3$ to $10^7$ colony forming units (CFU) were used for the test. Bacterial DNA was extracted from *Escherichia coli, Mycobacterium abscessus, Mycobacterium gordonae* and *Salmonella* Strains (*Salmonella typhimurium, Salmonella* Newport, and *Salmonella* Saintpaul) cultured for DTS analysis and Qiagen kit analysis.

For the genetic analysis of the bacterial genes, 2 µl of DNA extracted from the DTS analysis and the Qiagen kit analysis was amplified at 95° C. for 15 minutes using a total volume of 25 µl containing 1×PCR buffer (Qiagen, Hilden, Germany), 2.5 mM magnesium chloride (MgCl$_2$), 0.25 mM deoxynucleotide triphosphate, 25 pmol of each primer and 1 unit of Taq DNA polymerase; 45 cycles of 95° C., 30 seconds, 60° C., 30 seconds (*Mycobacterium abscessus,*

*Mycobacterium gordonae* and *Salmonella* strains) and 72° C., 30 seconds; and a final extension step at 72° C. for 7 minutes. PCR amplification products were visualized by gel electrophoresis in which the PCR product was separated on a 2% agarose gel containing ethidium bromide (EtBr) (Sigma-Aldrich). The gel was visualized using a Gel Doc System (Bio-Rad). Measurement of DNA concentration and purity was performed with a UV spectrophotometer (Perkin-Elmer).

<Example 5> DNA Extraction from Human Body Fluids Using DTS Analysis

To verify DTS analytical ability with human body fluids, 200 µl of body fluids (whole blood and urine) was introduced into the thin film device to extract DNA. First, an elution buffer and a body fluid sample containing proteinase K and DMS were respectively introduced into the previously prepared thin film device, and then transferred to a microchannel chamber to form a complex of DNA and DMA in the body fluid sample and DNA was extracted in the same manner as Example 2. At this time, the elution buffer and the body fluid sample were introduced into two different inlets at a flow rate of 1.5 ml/hr for 10 minutes using a syringe pump (KD Scientific, MA) and for the extraction and purification of DNA, the cartridge was incubated at 56° C. for 20 minutes. The flow rate of the inlet for PBS buffer inflow by the syringe pump was increased to 4 ml/hr for 10 minutes. Finally, the extracted DNA was eluted with 100 µl of elution buffer. Also, for comparison, 200 µl of whole blood or urine was used for genomic DNA extraction using a QIAmp DNA mini kit (Hilden, Germany). All extracted DNA was determined by UV spectrophotometer (Perkin-Elmer) according to DNA concentration and its purity.

<Example 6> Application of Homobifunctional Imidoesters for Nucleic Acids Extraction Using a Thin Film Microfluidic Platform (HINT Strategy)

The present inventors extracted and analyzed DNA from various samples including eukaryotic cells or prokaryotic cells through DTS (Dimethyl suberimidate/Thin film sample) analysis, which is a nucleic acids analysis using DMS in a thin film device through the preceding examples.

Figure 6:
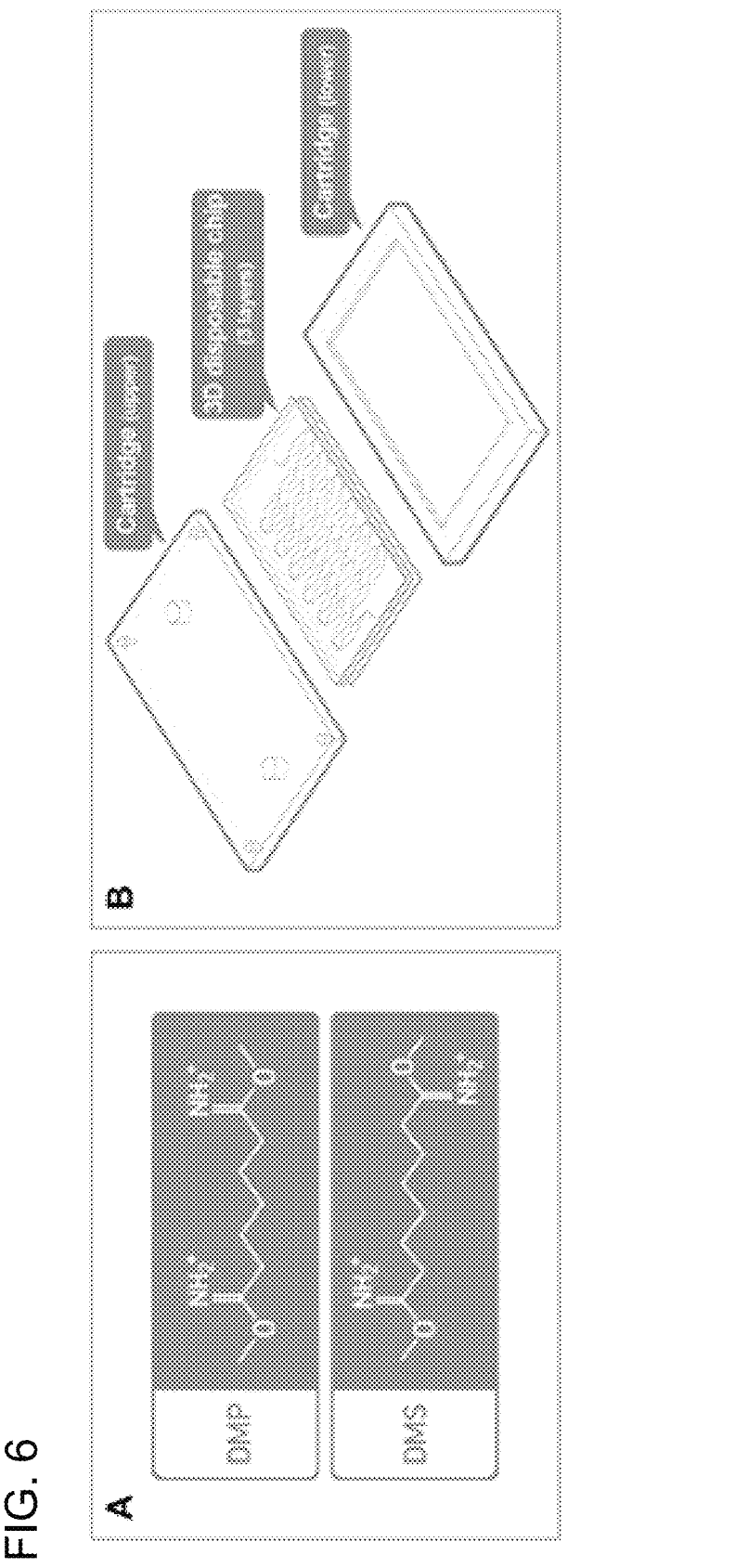
FIG. 6 is a view specially showing a micro fluid chamber.

The present inventors have also found that a HINT [homobifunctional imidoesters (HIs) for nucleic acids extraction using thin films] system which can extract RNA or DNA using a thin film-based microfluidic platform (FIG. 6). As the homobifunctional imidoesters (HIs), dimethylsuberimidate (DMS) and dimethylpimelimidate (DMP) was used and are composed of a methylene group and a bifunctional imidoester group (FIG. 6A). In thin film-based microfluidic platforms, sample lysis, washing and elution were performed on a single channel. In order to extract RNA or DNA from the sample using the HINT system, a sample mixture, a lysis buffer, and HIs (DMS or DMP) were pipetted into the system and the surface was activated with a reactive amine group beforehand and used to capture the nucleic acids and HIs complex (FIG. 6B). Thereafter, for RNA extraction, the reaction was carried out at room temperature for 10 to 20 minutes, and for DNA extraction, reaction was carried out at 56° C. for 20 minutes. After the reaction, the nucleic acids (RNA or DNA) could be extracted by washing and elution.

Figure 7:
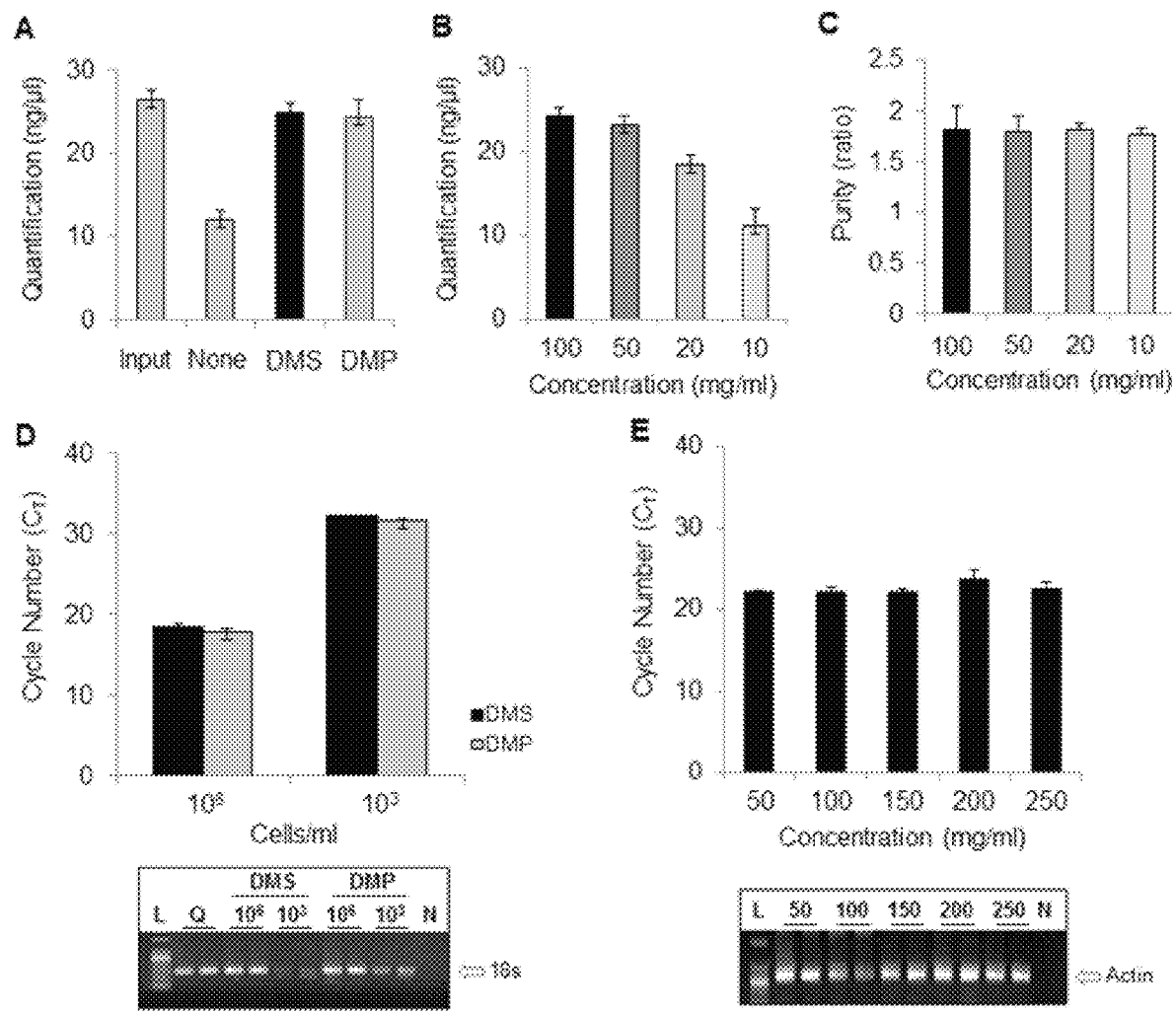
FIG. 7 shows the fundamental characterization of the HINT system for RNA and DNA extraction. (A) Recovery amounts of the input DNA (1 μg of human genomic DNA) with HIs [dimethyl suberimidate (DMS) or dimethyl pimelimidate (DMP)]. (B-C) The quantity (B) and purity (C) of the DNA extracted from the cells (HCT116, colorectal cancer cell line) using different concentration of DMS (100, 50, 20, and 10 mg/ml). (D) 18S gene amplification of RNA with two concentrations ($1\times10^3$ and $1\times10^6$) of RNA extracted from the system. (E) Actin gene amplification performed with DNA extracted from the system according to DMS concentration (50-250 mg/ml). L: DNA size marker, Q: RNA extracted with Qiagen kit, N: negative control.

Meanwhile, to confirm that the HINT system can be used to extract nucleic acids (RNA or DNA), basic characteristics of the system were confirmed in several cancer cell lines and bacterial cell lines. In FIG. 7A, the recovery of injected DNA (1 ug human genomic DNA) with and without HIs (DMS and DMP) was measured. At least 95% of DNA was recovered in both the DMS (black) and DMP (gray) experimental groups, and <50% DNA was recovered in the HIs-free experimental group (FIG. 7A). To optimize the system protocol for human genomic DNA or RNA extraction, cancer cell lines ($1\times10^6$ cells of breast cancer cell line (MCF7) or colorectal cancer cell line (HCT116)) were used. As an optimization method for extracting high quality and high capacity nucleic acids, the amount (FIG. 7B) and purity (FIG. 7C) of DNA extracted from cancer cells were measured by varying DMS concentrations (100, 50, 20, and 10 mg/ml). Unlike DNA extraction, RNA is generally more difficult to extract because it is easily degradable. To extract RNA at two concentrations of cancer cells ($1\times10^3$ and $1\times10^6$), DMS or DMP was applied to the HINT system. For PCR comparison experiments, 18S gene amplification was performed with two concentrations of RNA extracted from the system and single-step reverse transcription end-point PCR and single-step reverse transcription RT-PCR were performed. The 18S gene was strongly amplified at both the cell concentration of $10^6$ ($C_T$: 18.42±0.46 in DMS, $C_T$: 17.86±0.32 in DMP) and $10^3$ ($C_T$: 32.15±0.09 in DMS, $C_T$: 31.60±0.2 in DMP) (FIG. 7D). For the DNA extraction using the HINT system, two concentrations of cancer cells ($1\times10^3$ and $1\times10^6$) were used in combination with various concentrations of DMS (50-250 mg/ml). PCR For comparison, Actin gene amplification was performed with two concentrations of DNA extracted from the system, and end-point PCR and RT-PCR were performed (FIG. 7E). The Actin gene was amplified in $1\times10^6$ cells ($C_T$: 22.11±0.31; FIG. 7E) and $1\times10^3$ cells ($C_T$: 31.73±0.01) and amplified in all DMS conditions.

Figure 8:
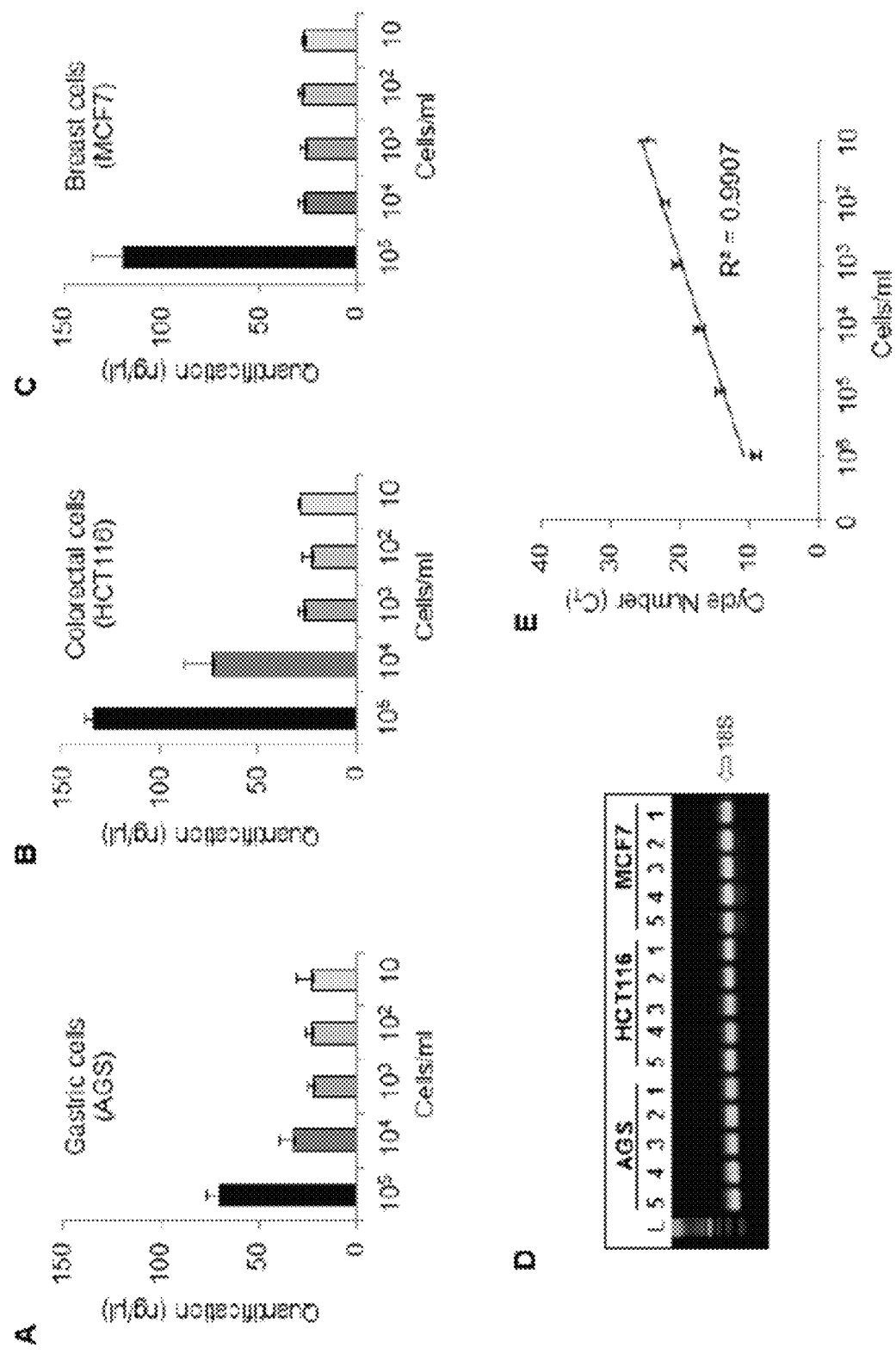
FIG. 8 shows application of the HINT system for RNA extraction with cancer cell lines. (A-C) Capacity of the HINT system with (A) AGS (gastric cancer cell line), (B) HCT116 (colorectal cancer cell line), and (C) MCF7 (breast cancer cell line) cells. (D) PCR amplification of 18S gene from extracted RNA. (E) Result of confirming cycle number ($C_T$) according to the concentration of HCT116 cells in single-step reverse transcription RT-PCR.

To further validate the HINT system in RNA extraction analysis, RNA was extracted and analyzed from three cancer cell lines, including AGS (gastric cancer cell line), HCT116 (colorectal cancer cell line) and MCF7 (breast cancer cell line) $1\times10^1$ to $1\times10^5$ cells were used through continuous dilution. It was confirmed that the amount of RNA extracted through the HINT system is dependent on the number of cells (FIG. 8A to FIG. 8C). As a result of PCR amplification of the 18S gene from the extracted RNA, it was confirmed that all the RNAs extracted from the three cancer cell lines were strongly amplified (FIG. 8D). FIG. 8E is a result of confirming the cycle number ($C_T$) according to the concentration of HCT116 cells in the single-step reverse transcription-RT-PCR. A high linearity ($R^2$=0.9907) was shown between $C_T$ and cell concentration.

Figure 9:
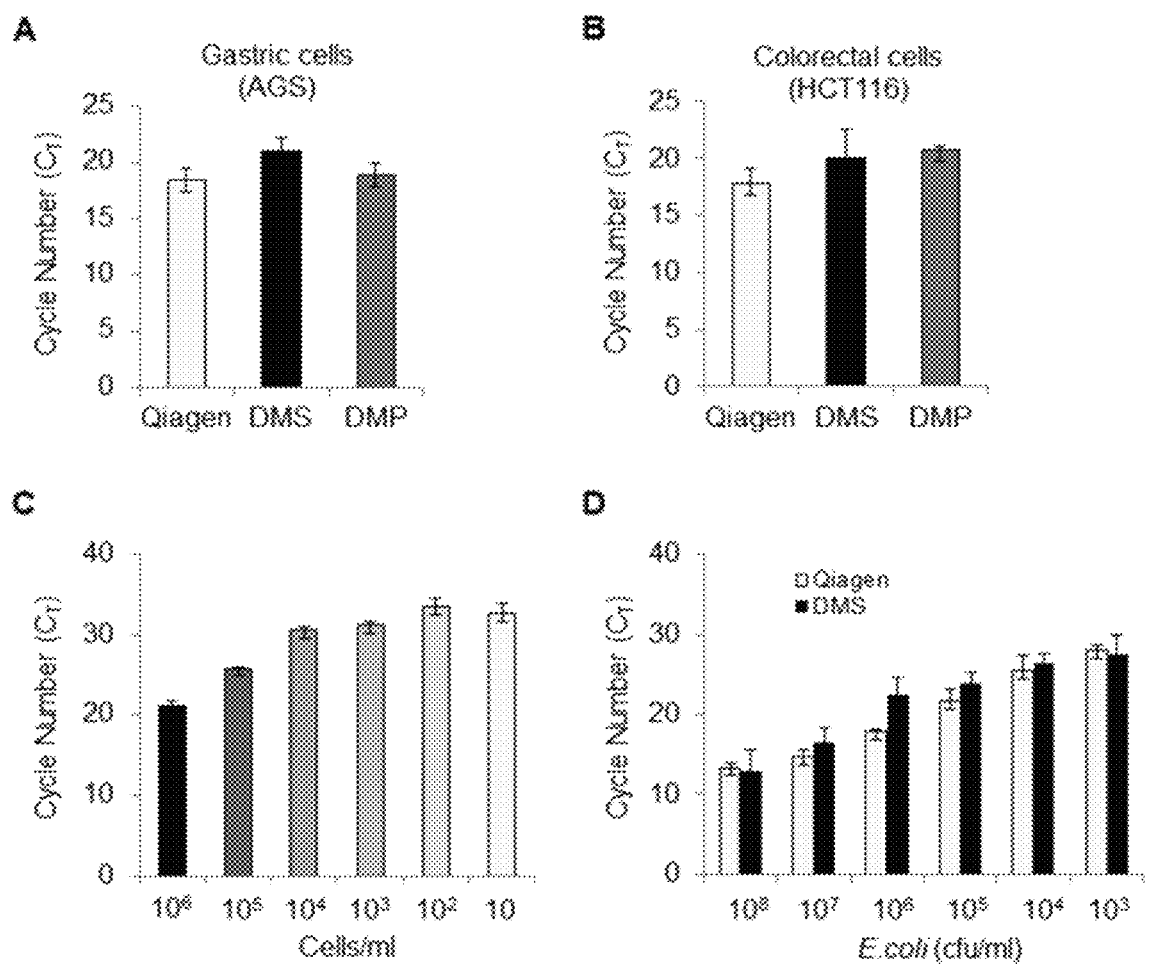
FIG. 9 shows application of the HINT system for DNA extraction with cancer cell lines. (A-B) The capacity of the HINT system with (A) AGS (gastric cancer cell line) and (B) HCT116 (colorectal cancer cell line) for DNA extraction. (C) Result of confirming the number of RT-PCR cycles of DNA extracted from HINT system by applying DMS according to the concentration of HCT116 cells. (D) RT-PCR analysis of DNA extracted from the HINT system with different *E. coli* concentrations.

To further validate the HINT system in DNA extraction assays, DNA was extracted from MCF7, AGS, and HCT116 cells for PCR analysis. The HINT system was compared with the Qiagen kit using the same concentration of cells ($1\times10^6$). The DNA extracted from the HINT system using AGS and HCT116 cells and DMS or DMP was equivalent to the amplification efficiency of DNA extracted from the Qiagen kit (FIG. 9A and FIG. 9B). Further, in RT-PCR, the DNA extracted from the HINT system using DMS or DMP was found to be dependent on the number of cells. The results of the experiment using DMS are shown in FIG. 9C. On the other hand, in order to confirm the applicability of the present system to various samples, bacterial DNA was extracted from E. coli and the cell concentration range was $1\times10^3$ to $1\times10^8$ CFUs. E. coli genes were strongly amplified in DNAs extracted from successively diluted samples. The DNA extracted from the HINT system had the same level of amplification efficiency as the DNA extracted from the Qiagen kit (FIG. 9D).

Also, in extracting viruses or bacterial nucleic acids (DNA and RNA) from mite-mediated disease samples such as severe fever with thrombocytopenia syndrome (SFTS) and scrub typhus (ST), it is confirmed if the HINT system can be applied. Using Qiagen kit and HINT system (using DMS), viral RNA was extracted from the plasma of SFTS patients. The RT-PCR amplification efficiency of the HINT system was not significantly different from the Qiagen kit (FIG. 10A). The RT-PCR amplification efficiency of the HINT system was found to be equivalent to that of the Qiagen kit as a result of extraction and analysis of bacterial DNA from the plasma of ST patients using Qiagen kit and HINT system (using DMS and DMP) (FIG. 10B).

On the other hand, a comparative experiment with DMA which is a compound similar to DMS and DMP used in the present invention, was performed. Using the HCT116 cancer cell line, DMA, DMS and DMP were added respectively, and DNA was extracted by the HINT system, and the amplification efficiency of the extracted DNA was compared. As shown in FIG. 11, it was confirmed in FIG. 11(A) that the amplification efficiency of DMS and DMP progressed rapidly by 2 cycles as compared with DMA, and when the efficiency for 2 cycles difference is confirmed, because in PCR, the amplification product is increased by 2 times per cycle in theory, when the expression level is compared, the difference of Ct value is found by the power of 2, and It was confirmed that the efficiency using DMP and DMS was about 4 times as high as that of DMA (FIG. 11B).

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method of extracting ribonucleic acid (RNA), comprising:

modifying a solid surface by introducing a silane compound and amine group to prepare an amine modified surface;

injecting a sample having $1\times10^1$ to $1\times10^3$ cells/ml and a compound represented by following Chemical Formula 2 or 3 into the amine modified surface, and forming a complex having the RNA within the sample and the compound; and extracting the RNA by adding an elution buffer to the amine modified surface on which the complex is formed, wherein proteinase K and DNase I are added to digest the proteins and the deoxyribonucleic acids (DNAs) prior to the step of extracting the RNA,

[Chemical Formula 2]

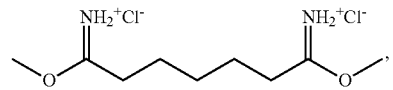

-continued

[Chemical Formula 3]

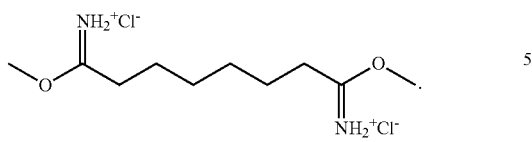

2. The method of claim 1, wherein the silane compound is 3-aminopropyltriethoxysilane (APTES).

3. The method of claim 1, further comprising washing the solid surface by plasma treatment before the modifying step.

4. The method of claim 1, wherein the sample is a eukaryotic cell, a bacterial cell, a virus cell, a whole blood or a urine derived sample.

5. The method of claim 1, further comprising treating a protease and the elution buffer on the amine modified surface, wherein the elution buffer is sodium bicarbonate.

* * * * *